United States Patent [19]
Marraccini et al.

[11] Patent Number: 4,801,409
[45] Date of Patent: Jan. 31, 1989

[54] HYPOFLUORITES AND BIS-HYPOFLUORITES, AND PROCESS FOR PREPARING SAME

[75] Inventors: Antonio Marraccini, Dormelletto; Giorgio Guglielmo, Mirano; Alessandro Malacrida, Sovico; Lamberto Roberti, Monza, all of Italy

[73] Assignee: Ausimont S.p.A., Milan, Italy

[21] Appl. No.: 93,700

[22] Filed: Sep. 8, 1987

[30] Foreign Application Priority Data

Sep. 10, 1986 [IT] Italy ................... 21658 A/86

[51] Int. Cl.$^4$ ........................... C07C 143/70
[52] U.S. Cl. ...................... 260/543 F; 560/300
[58] Field of Search ............... 260/543 F; 560/300

[56] References Cited

PUBLICATIONS

D. E. Gould et al, JACS, 191:61, 12 Mar. 1969, pp. 1310–1313.

Primary Examiner—Paul J. Killos
Attorney, Agent, or Firm—Stevens, Davis, Miller & Mosher

[57] ABSTRACT

Mono- and bis-hypofluorites respectively of formula: $FO_2S-R_f-CF_2OF$ and $FOCF_2-R'_f-CF_2OF$ wherein $R_f$ is perfluoroalkylene or perfluorochloroalkylene and $R'_f$ is a perfluoroalkylene or perfluorooxyalkylene, and process for preparing them, which is conducted continuously, at a temperature from 0° to 60° C. and comprises starting from the respective acyl fluorides

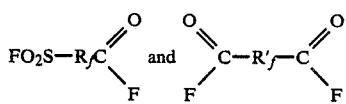

by reaction of fluorine in the gas phase in the presence of a catalyst consisting of K, Rb, Cs or Ba fluoride, preferably supported on a metal material.

9 Claims, No Drawings

HYPOFLUORITES AND BIS-HYPOFLUORITES, AND PROCESS FOR PREPARING SAME

The object of the present invention is an improved process for preparing hypofluorites and bis-hypofluorites by reaction of fluorine with starting compounds containing respextively one or two acyl fluoride groups

and the products so prepared.

The process is particularly suitable for preparing mono-hypofluorites containing a sulphonyl fluoride group —SO$_2$F, and represented by the following formula:

$$FO_2S—R_f—CF_2CO \quad (I)$$

wherein R$_f$ is a perfluoroalkylene radical or a fluorochloroalkylene radical having from 1 to 4 carbon atom and in particular selected from:

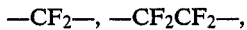

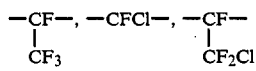

Starting compounds for preparing the hypofluorites of formula (I) are the corresponding acyl fluorides:

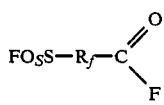

which, in turn, are easily preparable according to known methods based on the reaction of SO$_3$ with fluoroolefins (or fluorochloroolefins) or by electrochemical synthesis with generation of a sultone and subsequent opening of the sultone ring in the presence of basic catalysts, in particular alkaline fluorides or amines. Angew. Chemie Int. Ed. Vol. II (1972) No. 7, 583 and U.S. Pat. No. 4,466,881.

The process according to the present invention is also particularly suited to prepare bis-hypofluorites of perfluoroalkanes or perfluoroethers of general formula:

$$FOCF_2—R'_f—CF_2OF \quad (II)$$

where R'$_f$ is a perfluoroalkylene in particular from 1 to 8 carbon atoms —CF$_2$—, —CF$_2$CF$_2$—, or it represents a perfluoroxyalkylene radical in particular having from 1 to 10 carbon atoms and selected from —CF$_2$OCF$_2$CF$_2$— or (—CF$_2$O—CF$_2$CF$_2$—)$_2$.

Starting products are the corresponding acyl fluorides:

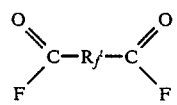

The latter are generally prepared by electrochemical fluorination of the corresponding dicarboxylic acids or from corresponding chlorides by reaction with KF in solvents (J.A.C.S. 89, 12 pages 2841-2843). As starting products, the acid difluorides of malonyl and of succinyl are particularly interesting. In the case of the compounds where R'$_f$ is an ethereal radical, the precursors are obtainable from the perfluoropolyether mixtures obtained in the C$_2$F$_4$ photooxidation process, by fractionated distillation.

Very few references to the preparation of bis-hypofluorites are contained in the technical literature. In particular, the article by J. H. Prager in J.O.C., February 1966, page 392 "1,3-bis-(fluoroxy)perfluoropropane and Other Oxygen-Containing Compounds by Direct Fluorination" describes the reaction of gaseous fluorine with fluorinated compounds containing a —OH group, said reaction given rise also to the compound:

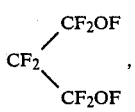

however with a yield of 2% beside 2% of mono-hypofluorite. It is clear that this process cannot be of practical interest.

The process of the present invention permits to obtain high yields of hypofluorites and bis-hypofluorites of the type indicated hereinbefore by means of a continuous process utilizable on a commercial scale.

The process according to the invention consists in reacting, in the gas phase, fluorine with an acyl fluoride of class

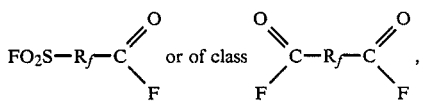

optionally with a little fluorine excess with respect to the stoichiometric amount, at a temperature ranging from 0° to 60° C. and preferably from 20° to 30° C., and in the presence of a solid catalyst composed of a fluoride of an alkaline or alkaline-earth metal, preferably selected from K, Rb, Cs and Ba, in particular CsF, preferably carried on or mixed with a metal.

The granulometry of the utilized catalyst is preferably in the range of from 250 to 500μ and it can be obtained by means of grinding. In any case, the granulometry is chosen so as to obtain a fixed bed.

Preferably, the catalysts is mixed with metal particles having dimensions of the order of few mm; the metal can be for example Cu, Ni, Fe or Al, in order to facilitate the heat exchange of the reactor.

The catalyst may be also preferably carried out on the indicated metal material, as is described in an earlier patent application of the Applicant. In particular, a method of preparing the catalyst consists in subjecting a copper oxide (CuO or Cu$_2$O or a mixture thereof) having the shape of small pieces or granules (beads, little cylinders and the like), to reduction with nitrogen-diluted hydrogen, at a temperature from 200° to 500° C., preferably from 250° to 350° C., so obtaining a metal copper carrier of porous nature and of specific surface, as is indicated in the above-cited patent application. This carrier is then impregnated with an alkaline fluoride solution, in particular a caesium fluoride solution. Generally, the amount of CsF that can be fixed on the carrier is rather high, up to about 10% by weight. Also amounts of 3% provide a good catalyst. At last, the solvent utilized is removed by evaporation under vacuum.

The catalyst so prepared exhibits a high yield, which is satisfactory even after a continuous very long running: in fact, after having been utilized for a few days, it does not exhibit a sensible decay. Furthermore, in the case that a regeneration should become necessary, it could be obtained in a very simple manner in the same reactor by means of a hydrogen stream at a temperature, for example of 200°–300° C.

Due to the high exothermicity and the high reaction velocity it is generally advisable, for an easier temperature control, to dilute the reagents with a proper inert gas, such as nitrogen or helium, or also with a chlorofluorohydrocarbon in the vapour state and inert under the reaction conditions, in particular $C_2F_4Cl_2$, $C_2F_5Cl$.

The reaction can be conducted at a pressure equal to or higher than the atmospheric pressure.

The reaction occurs with very short contact times, generally below 1 minute. The conversion is practically complete and the hypofluorite yield is very high, generally higher than 95%.

As is known, the hypofluorites are capable of reacting with fluorinated olefins to form ethers which, by consecutive reactions, provide fluorinated vinylethers. The latter, when obtained from the compouns of formula (I), i.e. when they contain the sulphonyl group, are utilizable as monomers in the preparation of polymeric substances (resins), which are useful as acid catalyst of insoluble nature or as a material for the production of ion-exchange membranes or diaphragms.

The bis-hypofluorites of general formula (II) can be utilized in the preparation of the corresponding bis-vinylethers (diglycidyl ethers) by reaction with fluorinated olefins of both hypofluorite groups, as mentioned hereinbefore.

In the reaction with fluoroolefins for the preparation of vinylethers it is possible to directly use the reaction mixture containing the inert diluent, if any, because the conversion of the starting product is generally total and the hypofluorite yield very high.

Some of the compounds according to the process of the invention are new, in particular the ones of the class of formula (I) wherein $R_f$ is —CFCl— or

the one of class (II) wherein $R'_f$ is —$CF_2O$—$CF_2CF_2$—, or (—$CF_2O$—$CF_2CF_2$—)$_2$.

The following examples are given merely to illustrate possible embodiments of the process according to the invention.

EXAMPLE 1

Preparation of 1-fluoroxy-2(fluorosulphonyl)-tetrafluoroethane

To an AISI 316 steel reactor having a diameter of 50 mm and a useful volume of 500 cm$^3$, filled with a catalyst prepared by mixing copper chips with 350 g of CsF, dried at 350° C. in a nitrogen flow during 4 hours, ground and subjected to screening in an anhydrous environment, a gaseous mixture consisting of $N_2/F_2/FO_2S$—$CF_2$—$C(O)F$ in a molar ratio of 1/1/1 was continuously fed at a total flowrate of 12 Nl/h (5.10$^{-4}$ moles/h per gram of catalyst for each reagent) and at a pressure of 1.1 atm. The reagent mixture had been previously purified from HF, H$_2$O possible impurities (alcohols). The temperature in the reactor was maintained at +20° C. by means of a thermostatic bath. The outflowing gaseous mixture, analyzed by IR spectrophotometry, NMR $^{19}$F and iodometry, revealed the presence of FO$_2$S—CF$_2$—CF$_2$OF. Conversion and yields were of about 100%.

The NMR analysis exhibited a typical signal of hypofluorites (δ, with respect to CFCl$_3$: +150 ppm); the IR band at 895 cm$^{-1}$ is typical of a hypofluorite.

Conversion of the reagents and yield remained unchanged also after a 10-hour run.

EXAMPLE 2

Into the reactor of example 1 there was continuously charged a gaseous mixture consisting of $N_2/F_2/FO_2S$—$CF_2$—$C(O)F$ in a molar ratio of 1/2/1, at a total flowrate of 8N 1/H (5.10$^{-4}$ moles/h of F$_2$ per gram of catalyst and 2.5.10$^{-4}$ moles/h of FO$_2$S—CF$_2$—C(O)F per gram of catalyst) and at a pressure of 1.1 atm. The temperature in the reactor was maintained at +30° C. by means of a thermostatic bath.

The outflowing mixture, subjected to IR spectrophotometric analysis and to iodometric analysis, showed a complete conversion of FO$_2$S—CF$_2$—C(O)F to FO$_2$S—CF$_2$—CF$_2$OF; in fact, the IR band between 6.8 and 7 micron was present and its intensity remained unchanged (typical band of —SO$_2$F); while the band between 5.3 and 5.5 micron (typical band of COF) was fully absent and a new band typical of group —CF$_2$OF appeared; ν (OF)=895 cm$^{-1}$.

EXAMPLE 3

Into the reactor of example 1 there was continuously charged a gaseous mixture consisting of

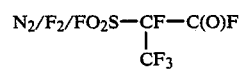

in a molar ratio of reagents 1.2/1, at a total flowrate of 8N 1/h and at a pressure of 1.1 atm. The temperature in the reactor was maintained at +20° C. by means of a thermoplastic bath.

The outflowing mixture, subjected to IR spectrophotometric analysis and to iodometric analysis, showed a complete conversion of

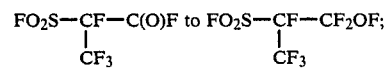

in fact, the IR band between 6.8 and 7 micron was present and its intensity remained unchanged (typical band of —SO$_2$F); while the band between 5.3 and 5.5 micron (typical band of COF) was fully absent and a new band centered at about 887 cm$^{-1}$ attributed to —CF$_2$OF appeared. The NMR analysis exhibited a typical signal of hypofluorites (δ, with respect to CFCl$_3$: +157.7 ppm).

EXAMPLE 4

Into the reactor of example 1 there was continuously charged a gaseous mixture consisting of $N_2/F_2/FOC-CF_2-CF_2-COF$ in a molar ratio of reagents of 2.5 1, at a total flowrate of 8N 1/h and at a pressure of 1.1 atm. The temperature in the reactor was maintained at $+20°$ C. by means of a thermostatic bath.

The outflowing mixture, subjected to IR spectrophotometric analysis and to iodometric analysis, showed good conversion, of $FOC-CF_2-CF_2-COF$ to $FOCF_2-CF_2-CF_2-CF_2OF$ in fact, the IR band between 5.3 and 5.5 micron (typical band of COF) was nearly absent and a new band typical of group $-CF_2OF$ appeared.

What we claim is:

1. A process for preparing hypofluorites and bis-hypofluorites, respectively of formula:

$$FSO_2-R_f-CF_2OF \qquad (I)$$

and $$FOCF_2-R'_f-CF_2OF \qquad (II)$$

wherein $R_f$ is a perfluoroalkylene or a perfluorochloroalkylene having from 1 to 4 carbon atoms and $R'$ is a perfluoroalkylene or a perfluorooxyalkylene having from 1 to 10 carbon atoms, by reaction of the respective acid fluorides

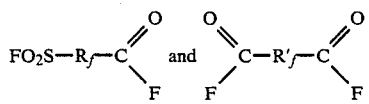

with fluorine, in the gas phase, conducted at 0°–60° C. in the presence of a catalyst composed of a K, Rb, Cs or a Ba fluoride, preferably supported on a metal material and arranged in the reactor in the form of a fixed catalytic bed, the process being conducted continuously.

2. The process according to claim 1, wherein hypofluorites of formula (I) are prepared, in which $R_f$ is $-CF_2-$, $-CF_2CF_2-$, $$-CF-,\ -CFCl-,\ -CF- \atop \phantom{-CF-,\ }CF_3\phantom{-CFCl-,\ }CF_2Cl$$

and of formula (II) where $R'_f$ is $-CF_2-$, $-CF_2CF_2-$, $-CF_2OCF_2CF_2-$ or $(-CF_2O-CF_2CF_2-)_2$.

3. The process according to claim 1, wherein the reagents are diluted with an inert gas such as nitrogen or helium or with vapour of a chlorofluorohydrocarbon which is inert under the reaction conditions.

4. The compound of formula (I) wherein $R_f$ is $-CFCl-$.

5. The compound of formula (I) wherein $R_f$ is $$-CF- \atop CF_2Cl$$

6. The compound of formula (II) wherein $R'_f$ is $-CF_2O-CF_2CF_2-$.

7. The compound of formula (II) wherein $R'_f$ is $(-CF_2O-CF_2CF_2-)_2$.

8. Compounds having formula $$FSO_2R_fCF_2OF \qquad (I)$$

prepared by the process of claim 1.

9. Compounds having formula $$FO-CF_2-R'_f-CF_2OF \qquad (II)$$

prepared by the process of claim 1.

* * * * *